(12) United States Patent
Carlson et al.

(10) Patent No.: US 8,859,735 B2
(45) Date of Patent: Oct. 14, 2014

(54) GELATIN ALKYD PEPTIDES AND USES THEREOF

(75) Inventors: William B. Carlson, Seattle, WA (US); Vincenzo Casasanta, III, Woodinville, WA (US); Gregory David Phelan, Cortland, NY (US)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 13/885,306

(22) PCT Filed: Aug. 27, 2012

(86) PCT No.: PCT/US2012/052465
§ 371 (c)(1),
(2), (4) Date: May 14, 2013

(87) PCT Pub. No.: WO2014/035364
PCT Pub. Date: Mar. 6, 2014

(65) Prior Publication Data
US 2014/0057053 A1    Feb. 27, 2014

(51) Int. Cl.
*C07K 14/78* (2006.01)
*C09H 3/00* (2006.01)
*C08H 1/06* (2006.01)
*C09D 189/06* (2006.01)

(52) U.S. Cl.
CPC ...... *C07K 14/78* (2013.01); *C08H 1/06* (2013.01); *C09D 189/06* (2013.01)
USPC ............ 530/354; 106/31.54; 106/160.1

(58) Field of Classification Search
CPC ......... C09H 9/00; A61K 8/65; A61K 38/014; A61K 47/42; C07K 14/00
See application file for complete search history.

(56) References Cited

U.S. PATENT DOCUMENTS

| | | |
|---|---|---|
| 2,363,892 A | 11/1944 | Jean Baptiste Monier |
| 6,544,951 B2 | 4/2003 | Karanewsky et al. |
| 7,176,185 B2 | 2/2007 | Hilfinger et al. |
| 8,158,754 B2 * | 4/2012 | Song .......................... 530/354 |
| 8,232,371 B2 | 7/2012 | Cho et al. |
| 2003/0108885 A1 | 6/2003 | Schultz et al. |
| 2008/0051317 A1 | 2/2008 | Church et al. |

FOREIGN PATENT DOCUMENTS

WO    WO 2005012356 A2 *    2/2005

OTHER PUBLICATIONS

Cole et. al. Gelatin, Encyclopedia of Food Science and Technology, 2nd edition. 4 Vols. New York: John Wiley & Sons, 2000. 1183-1188.*
Goswami, T.H., et al., "Biodegradability of cured gelatin-PF resin blends by strains of *Aeromonas hydrophila* PC5 and LA8, a psychrotrophic bacterium," Sep. 1996, *Poly Deg. Stab.*, vol. 53, No. 3, pp. 273-277.
Goswami, T.H., et al., "Biodegradability of gelatin-PF resin blends by soil burial method," 1998, *Poly Deg. Stab.*, vol. 61, No. 2, pp. 355-359.
L. J. Calbo et al., "Handbook of Coatings Additives," 1987, pp. 496-506.
Russell, I.W., et al., "The Application of a Gelatin Resin System to Aerospace Expandable Sandwich Structures, Phase 1," Oct. 1965, *Technical Report AFAPL-TR-65-84*, Air Force Aero Propulsion Laboratory Research and Technology Division, Air Force Systems Command, Wright-Patterson Air Force Base, Ohio, 118 pp.
International Search Report and Written Opinion for Intl. Pat. Appln. No. PCT/US2012/052465, mailed on Nov. 2, 2012, 10 pp.

* cited by examiner

*Primary Examiner* — James H Alstrum Acevedo
*Assistant Examiner* — Jeanette Lieb
(74) *Attorney, Agent, or Firm* — Foley & Lardner LLP

(57) ABSTRACT

Polypeptides are provided, where the polypeptides include one or more groups of formula $-R^1-C(O)R^2$, where $R^1$ is an amino acid side chain, $R^2$ is a $C_8$-$C_{24}$ polyunsaturated alkenyl group, and the polypeptide is a gelatin.

30 Claims, No Drawings

GELATIN ALKYD PEPTIDES AND USES THEREOF

CROSS-REFERENCE TO RELATED APPLICATIONS

This application is a U.S. national phase application of International Application Serial No. PCT/US2012/052465, filed on Aug. 27, 2012, the entire contents of which is hereby incorporated herein by reference for all purposes in its entirety as if fully set forth herein.

FIELD

The present technology relates to gelatin alkyd peptides and articles made from such gelatin alkyd peptides.

BACKGROUND

The following description is provided to assist the understanding of the reader. None of the information provided or references cited is admitted to be prior art to the present technology.

An alkyd is a polyester modified by the addition of fatty acids and other components. Alkyd resins are commonly used as binders for ambient-cure, solvent-based coatings. The curing of solvent-borne alkyd resins is accomplished via autooxidative crosslinking of the alkyd film. Crosslinking occurs when the activated methylene groups in the unsaturated fatty acids or oils of the alkyd are oxidized in air to give hydroperoxides which subsequently decompose to generate free radicals, resulting in oxidative crosslinking. This oxidative crosslinking process is commonly accelerated by adding driers, such as, for example, various salts of cobalt, zirconium, calcium, and manganese. Although useful, most alkyd resins are poorly biodegradable and potentially harmful to the environment. Consequently, there is a need among producers of the alkyd resins for improved coatings that satisfy consumer needs but are non-toxic and biodegradable.

SUMMARY

The present technology provides gelatin alkyd peptides that can be used as coatings or epoxy resins for incorporation into a variety of products such as packaging materials and food containers. The gelatin alkyd peptides can also be used as thermoplastic materials for incorporation into such products. The gelatin alkyd peptides have $C_8$-$C_{24}$ polyunsaturated alkenyl groups that form crosslinks, and, thus, fortify the polymer. Importantly, the polymers are made from non-toxic natural products, gelatin and fatty acids, that are readily biodegradable, environmentally benign, and suitable for applications related to the food and beverage industry.

In one aspect, a polypeptide derivative is provided, where two or more amino acid side chains of the polypeptide derivative are each substituted with a $C_8$-$C_{24}$ polyunsaturated alkenyl group, and the polypeptide derivative is a gelatin. The polypeptide derivative is, of course, a polypeptide itself. Accordingly, in one embodiment, the polypeptide includes one or more groups of formula —$R^1$—$C(O)R^2$, where $R^1$ is an amino acid side chain, and $R^2$ is a $C_8$-$C_{24}$ polyunsaturated alkenyl group, and the polypeptide is a gelatin. In some embodiments, the polypeptide has at least one intramolecular crosslink, where each intramolecular crosslink includes two $R^2$ groups within the polypeptide that are joined by a bond, O, O—O, or a combination thereof. In other embodiments, the polypeptide has at least one intermolecular crosslink, where each intermolecular crosslink includes a first $R^2$ group from the polypeptide and a second $R^2$ group from another such polypeptide, where the first and second $R^2$ groups are joined by a bond, O, O—O, or a combination thereof.

In some embodiments, the $C_8$-$C_{24}$ polyunsaturated alkenyl groups are derived from a fatty acid, where the fatty acid is hexadecatrienoic acid, linoleic acid, α-linolenic acid, stearidonic acid, eicosatrienoic acid, eicosatetraenoic acid, eicosapentenoic acid, heneicosapentenoic acid, docosapentenoic acid, docosahexaenoic acid, tetracosapentenoic acid, tetracosahexaenoic acid, or a combination thereof. In some embodiments, the $C_8$-$C_{24}$ polyunsaturated alkenyl groups are in an all-cis configuration and are derived from omega-3 fatty acids.

In another aspect, a composition is provided where the composition includes a polypeptide, where the polypeptide includes two or more groups of formula —$R^1$—$C(O)R^2$, $R^1$ is an amino acid side chain, $R^2$ is a $C_8$-$C_{24}$ polyunsaturated alkenyl group, the polypeptide is a gelatin, and where the composition includes at least one drier, pigment, leveling agent, flatting agent, dispersing agent, flow control agent, ultraviolet (UV) absorber, or a combination thereof.

In another aspect, an article is provided where the article includes a polypeptide, where the polypeptide includes two or more groups of formula —$R^1$—$C(O)R^2$, $R^1$ is an amino acid side chain, $R^2$ is a $C_8$-$C_{24}$ polyunsaturated alkenyl group, the polypeptide is a gelatin, and where the article includes packaging for a comestible, such as a coating, a can, a box, a tray, a liner, or a wrapper.

A method is also provided for coating an article. The method includes contacting the article with a polypeptide, where the polypeptide includes two or more groups of formula $R^1$—$C(O)R^2$, where $R^1$ is an amino acid side chain, $R^2$ is a $C_8$-$C_{24}$ polyunsaturated alkenyl group, and the polypeptide is a gelatin; and exposing the article to air until at least two $R^2$ groups are crosslinked by a bond, O, O—O, or a combination thereof, to form the coated article.

The foregoing summary is illustrative only and is not intended to be in any way limiting. In addition to the illustrative aspects, embodiments and features described above, further aspects, embodiments and features will become apparent by reference to the following drawings and the detailed description.

DETAILED DESCRIPTION

The illustrative embodiments described in the detailed description and claims are not meant to be limiting. Other embodiments may be utilized, and other changes may be made, without departing from the spirit or scope of the subject matter presented here.

The present technology is described herein using several definitions, as set forth throughout the specification.

As used herein, unless otherwise stated, the singular forms "a," "an," and "the" include plural reference. Thus, for example, a reference to "a monomer" includes a plurality of monomers, and a reference to "an article" is a reference to one or more articles.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Alkyl groups include straight chain, branched chain, or cyclic alkyl groups having 1 to 24 carbons or the number of carbons indicated herein. In some embodiments, an alkyl group has 1 to 16 carbon atoms, 1 to 12 carbons, 1 to 8 carbons or, in some embodiments, 1 to 6, or 1, 2, 3, 4 or 5 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, isobutyl, sec-butyl, tert-butyl, neopentyl, isopentyl, and 2,2-dimethylpropyl groups. In some embodiments, the alkyl groups may be substituted alkyl groups.

Alkenyl groups include straight and branched chain alkyl groups as defined above, except that at least one double bond exists between two carbon atoms. Thus, alkenyl groups have 2 to 24 carbon atoms, 2 to 10 carbons or, in some embodiments, 2 to 8, 2 to 6, or 2 to 4 carbon atoms. Examples include, but are not limited to vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, among others. Representative substituted alkenyl groups may be mono-substituted or substituted more than once, such as, but not limited to, mono-, di- or tri-substituted with substituents such as those listed above.

The term "amine" (or "amino") as used herein refers to —NHR and —NRR' groups, where R, and R' are independently hydrogen, or a substituted or unsubstituted alkyl, alkenyl, alkynyl, cycloalkyl, aryl or aralkyl group as defined herein. Examples of amino groups include —NH$_2$, methylamino, dimethylamino, ethylamino, diethylamino, propylamino, isopropylamino, phenylamino, benzylamino, and the like.

The term "oxo" refers to a divalent oxygen group. While the term includes doubly bonded oxygen, such as that found in a carbonyl group, as used herein, the term oxo explicitly includes singly bonded oxygen of the form —O— which is part of a polymer backbone. Thus, an oxo group may be part of an ether linkage (—O—), an ester linkage (—O—C(O)—), a carbonate linkage (—O—C(O)O—), a carbamate linkage (—O—C(O)NH— or —O—C(O)NR—), and the like.

"Substituted" refers to a chemical group as described herein that further includes one or more substituents, such as lower alkyl (including substituted lower alkyl such as haloalkyl, hydroxyalkyl, aminoalkyl), aryl (including substituted aryl), acyl, halogen, hydroxy, amino, alkoxy, alkylamino, acylamino, thioamido, acyloxy, aryloxy, aryloxyalkyl, carboxy, thiol, sulfide, sulfonyl, oxo, both saturated and unsaturated cyclic hydrocarbons (e.g., cycloalkyl, cycloalkenyl), cycloheteroalkyls and the like. These groups may be attached to any carbon or substituent of the alkyl or alkenyl moieties. Additionally, the substituents may be pendent from, or integral to, the carbon chain itself.

The term "fatty acid," as used herein, refers to a carboxylic acid having any C$_8$-C$_{24}$ polyunsaturated alkenyl group, C$_8$-C$_{24}$ monounsaturated alkenyl group, or a C$_8$-C$_{24}$ alkyl group.

The term "omega-3 fatty acid," (also called ω-3 fatty acid or n-3 fatty acid) includes fats commonly found in marine and plant oils. Omega-3 fatty acid are polyunsaturated fatty acids with a double bond (C=C) starting after the third carbon atom from the end of the carbon chain. The location of the first double bond is counted from the methyl end, which is also known as the omega (ω) end or the n end.

The terms "thermoplastic" and "thermoplastic material," as used herein, refer to thermoplastic polymers known in the art, including polymers including at least one of a polyacrylate, a polymethacrylate, a polyolefin, a polyepoxy, a polyurethane, or a polyurea. In some embodiments the thermoplastic is made from any of the gelatin alkyd peptides described herein or a copolymer including any of the gelatin alkyd peptides described herein and at least one of a polyacrylate, a polymethacrylate, a polyolefin, a polyepoxy, a polyurethane, or a polyurea.

The term "gelatin," as used herein, refers to a mixture of peptides and proteins produced by partial hydrolysis of collagen extracted from the skin, boiled crushed bones, connective tissues, organs and some intestines of animals such as domesticated cattle, chicken, and pigs. Gelatin melts to a liquid when heated and solidifies when cooled again. Aqueous gelatin forms a semi-solid colloid gel. Gelatin forms a high viscosity solution with warm water, which sets to a gel on cooling. The chemical composition of gelatin is, in many respects, similar to that of collagen. Gelatin is unusually high in the non-essential amino acids glycine and proline (i.e., those produced by the human body), while lacking certain essential amino acids (i.e., those not produced by the human body). It contains no tryptophan and is deficient in isoleucine, threonine, and methionine. In some embodiments, the gelatin derivatives described herein can have about 21% glycine, about 12% proline, about 12% hydroxyproline, about 10% glutamic acid, about 9% alanine, about 8% arginine, about 6% aspartic acid, about 4% lysine, about 4% serine, about 3% leucine, about 2% valine, about 2% phenylalanine, about 2% threonine, about 1% isoleucine, about 1% hydroxylysine, about <1% methionine, about <1% histidine and/or about <0.5% tyrosine, wherein the percentage refers to the approximate number of each amino acid residue in the polypeptide relative to the total number of amino acid residues in the polypeptide.

The terms "gelatin alkyd" and "gelatin alkyd peptide," and "polypeptide," as used herein, refer to a gelatin peptide having amino acid side chains that are covalently attached, via amide or ester linkages, to fatty acids having C$_8$-C$_{24}$ polyunsaturated alkenyl groups and, optionally, C$_8$-C$_{24}$ monounsaturated alkenyl groups and/or C$_8$-C$_{24}$ alkyl groups. Crosslinking of their C$_8$-C$_{24}$ polyunsaturated alkenyl groups, can be achieved by air curing.

Gelatin alkyd resins can be classified by the oil length, which is the number of grams of oil used to make 100 grams of resin (also defined as the percent oil in the resin). Short oil gelatin alkyd resins have less than about 45 wt. % oil, medium oil resins have between about 45 wt. %-55 wt. % oil and long oil resins have more than about 55 wt. % oil. As is known in the art, longer chain lengths in the oils generally result in lower resin viscosity, decreased resin hardness, decreased water resistance and increased film flexibility.

A polypeptide is provided for use as a thermoplastic material, coating, adhesive, or epoxy resin for incorporation into a variety of products such as packaging materials and food containers. The polypeptide has C$_8$-C$_{24}$ polyunsaturated alkenyl groups that form cross-links, and, thus, fortify the peptide. In any of the embodiments, the polypeptide may be a gelatin alkyd peptide. The polypeptides are based upon natural materials and therefore pose no, or at least only a limited, toxic risk to those in contact with such materials. Thus, they are environmentally friendly. For example, a polypeptide is provided, where the polypeptide includes one or more groups of formula —R$^1$—C(O)R$^2$, where R$^1$ is an amino acid side chain, R$^2$ is a C$_8$-C$_{24}$ polyunsaturated alkenyl group, and the polypeptide is a gelatin. In some embodiments, the polypeptide further includes one or more groups of formula —R$^1$—C(O)R$^3$, where R$^3$ is a C$_8$-C$_{24}$ monounsaturated alkenyl group, C$_8$-C$_{24}$ alkyl group, or a combination thereof.

The polypeptides are illustrated in Scheme 1, which illustrates a preparative procedure and illustrates one embodiment. In Scheme 1, gelatin derivative 1.5 is prepared from peptide 1.1. Various materials may be used to incorporate R$_1$, the polyunsaturated alkenyl group, as illustrated by 1.2, 1.3, and 1.4. The modification of a single amino acid side (lysine) is illustrated below. However, numerous amino chains within the peptide may be modified by this procedure.

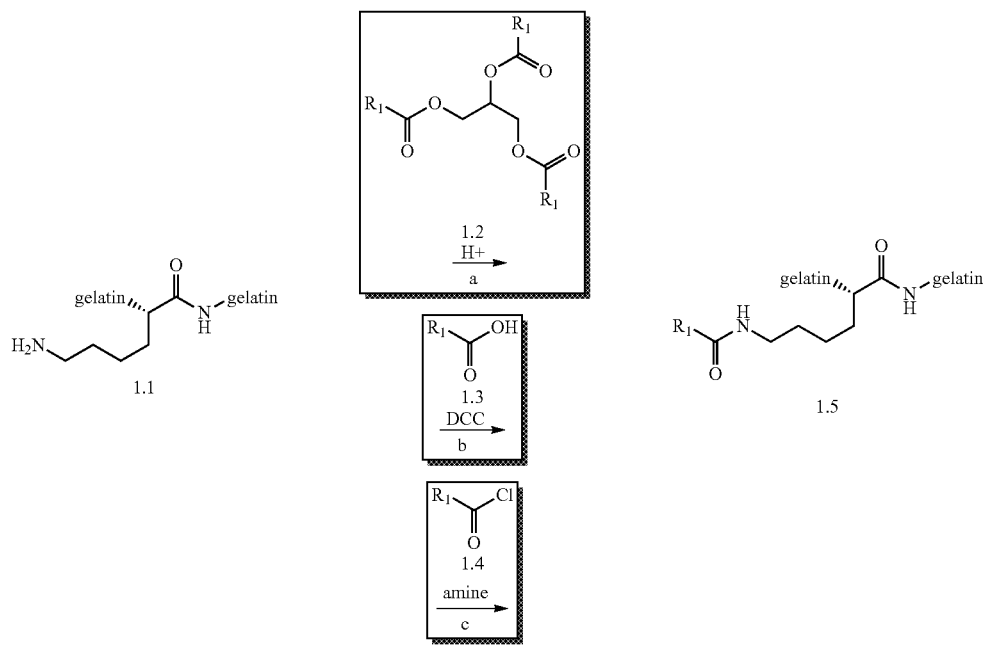

Scheme 1

The polyunsaturated alkenyl groups provide unsaturated functionality that provide a basis for intra- and/or inter-molecular cross-linking of the polypeptides. The cross-linking that occurs is based upon the curing of other alkyl oils, whereupon exposure to heat, air, or both heat and air, the oils cure to form a coating. Here the polypeptide provides for a backbone to the materials, such that larger polymer may be formed. In some embodiments, the polypeptide has at least one intramolecular crosslink, where each intramolecular crosslink includes two $R^2$ groups within the polypeptide that are joined by a bond, O, O—O, or a combination thereof. In other embodiments, the polypeptide has at least one intermolecular crosslink, where each intermolecular crosslink includes a first $R^2$ group from the polypeptide and a second $R^2$ group from another such polypeptide, where the first and second $R^2$ groups are joined by a bond, O, O—O, or a combination thereof.

In some embodiments, at least two of the $C_8$-$C_{24}$ polyunsaturated alkenyl groups appended to the peptide are crosslinked by a bond, O, O—O, or a combination thereof. In some embodiments, at least two of the crosslinked $C_8$-$C_{24}$ polyunsaturated alkenyl groups include:

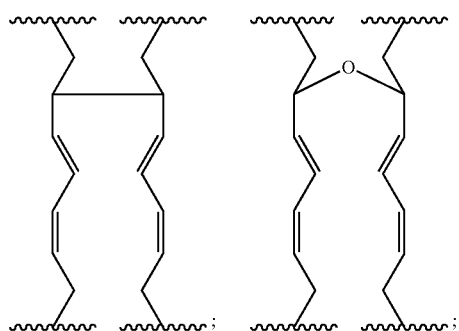

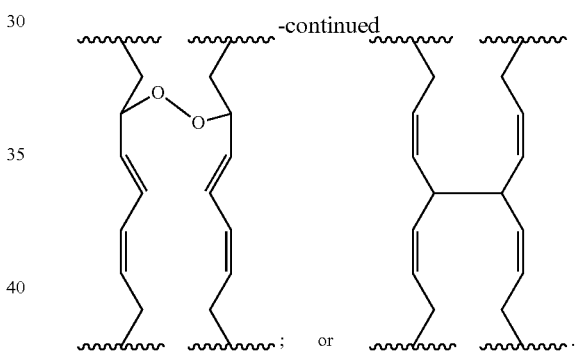

In some embodiments, substituent —C(O)$R^2$ includes a $C_8$-$C_{24}$ polyunsaturated alkenyl group. Substituent —C(O)$R^2$, and the $C_8$-$C_{24}$ polyunsaturated alkenyl group, derive from a fatty acid, with the fatty acid reacting with the hydroxyl, thiol, or amino group of the amino acid side chain within polypeptide. Representative fatty acids having $C_8$-$C_{24}$ polyunsaturated alkenyl groups include, but are not limited to, hexadecatrienoic acid, linoleic acid, α-linolenic acid, stearidonic acid, eicosatrienoic acid, eicosatetraenoic acid, eicosapentenoic acid, heneicosapentenoic acid, docosapentenoic acid, docosahexaenoic acid, tetracosapentenoic acid, and tetracosahexaenoic acid. In some embodiments, the fatty acid includes linoleic acid or α-linolenic acid. Combinations of any two or more fatty acids may also be employed.

In some embodiments, the $C_8$-$C_{24}$ polyunsaturated alkenyl groups are all-cis $C_8$-$C_{24}$ polyunsaturated alkenyl groups. In some embodiments, —C(O)$R^2$ and the all-cis $C_8$-$C_{24}$ polyunsaturated alkenyl group are derived from omega-3 fatty acids.

The $C_8$-$C_{24}$ polyunsaturated alkenyl groups may be in an all-cis configuration. That is a configuration where each site of unsaturation is in a cis conformation. Thus, in some embodiments, the polypeptide includes —C(O)$R^2$ which derives from an all-cis $C_8$-$C_{24}$ polyunsaturated alkenyl group. All cis-$C_8$-$C_{24}$ polyunsaturated alkenyl groups include, but are not limited to, those that are derived from all-cis-7,10,13-hexadecatrienoic acid, all-cis-9,12-linoleic acid, all-cis-9,12,15-octadecatrienoic acid, all-cis-6,9,12,15-octadecatetraenoic acid, all-cis 11,14,17 eicosatrienoic acid, all-cis-8,11,14,17-eicosatetraenoic acid, all-cis-5,8,11,14,17-eicosapentenoic acid, all-cis-6,9,12,15,18-heneicosapentenoic acid, all-cis-7,10,13,16,19-docosapentenoic acid, all-cis-4,7,10,13,16,19-docosahexaenoic acid, all-cis-9,12,15,18,21-tetracosapentenoic acid, and all-cis-6,9,12,15,18,21-tetracosahexaenoic acid. In some embodiments, the all-cis $C_8$-$C_{24}$ polyunsaturated alkenyl groups are derived from all-cis-9,12-linoleic acid or all-cis-9,12,15-octadecatrienoic acid. The $C_8$-$C_{24}$ all-cis acids may include any combination of any two or more such acids.

In addition to including a cross-linking basis, the $C_8$-$C_{24}$ polyunsaturated alkenyl groups increase the hydrophobicity of the polypeptides. Cross-linking of the $C_8$-$C_{24}$ polyunsaturated alkenyl groups within the polypeptide also imparts rigidity to the polypeptide.

$C_8$-$C_{24}$ monounsaturated alkenyl groups, and/or $C_8$-$C_{24}$ alkyl groups may also be incorporated into the polypeptide to reduce the amount of cross-linking and therefore reduce the rigidity of the polypeptide. In some embodiments, one or more amino acid side chains of the polypeptide are each substituted with a $C_8$-$C_{24}$ monounsaturated alkenyl group, a $C_8$-$C_{24}$ alkyl group, or a combination thereof. Thus, in some embodiments, the polypeptide includes one or more groups of formula —$C(O)R^3$, where $R^3$ is a $C_8$-$C_{24}$ monounsaturated alkenyl group, $C_8$-$C_{24}$ alkyl group, or a combination thereof. Such $C_8$-$C_{24}$ monounsaturated alkenyl groups may be derived from a fatty acid. Representative non-limiting fatty acids having $C_8$-$C_{24}$ monounsaturated alkenyl groups include, but are not limited to, oleic acid. In some embodiments, —$C(O)R^3$ derives from oleic acid, palmitoleic acid, and vaccenic acid. Representative non-limiting fatty acids having $C_8$-$C_{24}$ alkyl groups include, but are not limited to, lauric acid, myristic acid, palmitic acid, and stearic acid. In some embodiments, —$C(O)R^3$ derives from lauric acid, myristic acid, palmitic acid, or stearic acid.

As implied by the name, the polypeptide contains a backbone that includes a variety of amino acid residues. The amino acids that are found in gelatin are listed above, however, the amino acids and amounts of the amino acids in the polypeptide may be varied. For example, in some embodiments, the polypeptide includes about 5 wt % to about 20 wt % hydroxyproline. This may include any individual amount as well, for example, the polypeptide may include about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, about 20 wt % hydroxyproline, and fractional amounts between any two of these values.

The polypeptide may have a weight average molecular weight (Mw) of from about 1,000 Daltons to about 500,000 Daltons. In some embodiments, the polypeptide has a Mw of about 50,000 Daltons to about 400,000 Daltons. In some embodiments, the polypeptide has a Mw of about 50,000 Daltons to about 300,000 Daltons. In some embodiments, the polypeptide has a Mw of about 50,000 Daltons to about 200,000 Daltons. In some embodiments, the polypeptide has a Mw of about 50,000 Daltons to about 100,000 Daltons. Specific examples of Mw include about 1,000 Daltons, about 5,000 Daltons, about 25,000, about 50,000 Daltons, about 100,000 Daltons, about 250,000 Daltons, about 500,000 Daltons, and ranges between any two of these values.

The $C_8$-$C_{24}$ polyunsaturated alkenyl group is covalently attached via an amide, ester, or thioester linkage to an amino acid side chain of the polypeptide, formed by reaction of an amine, hydroxyl, or thiol group of an amino acid side chain in the polypeptide with the acid of the fatty acid. The amino acid may be any of the naturally occurring or synthetic amino acids. For example, the amino acid may be lysine, arginine, histidine, serine, threonine, asparagine, glutamine, cysteine, selenocysteine, tyrosine, or tryptophan. Consequently, substituent $R^1$ of the polypeptide described herein can be an amino acid side chain from lysine, arginine, histidine, serine, threonine, asparagine, glutamine, cysteine, selenocysteine, tyrosine, or tryptophan. In some embodiments, substituent $R^1$ of the polypeptide described herein is the amino acid side chain from lysine. A fraction or all of the amino acids in the polypeptide may be reacted with the fatty acids to form the polypeptides described herein. Thus, from about 5% to 100% of the amino acids may be reacted with the fatty acids. This includes, from about 10% to about 90% of the amino acids may be reacted with the fatty acids. In some embodiments, from about 5% to 100% of the lysine, arginine, histidine, serine, threonine, asparagine, glutamine, cysteine, selenocysteine, tyrosine, or tryptophan groups in the polypeptide, or in the gelatin, are substituted with $C_8$-$C_{24}$ polyunsaturated alkenyl groups. In some embodiments, at least 10% of all the lysine side chains within the polypeptide are substituted with —$C(O)R^2$, —$C(O)R^3$, or a combination thereof. In other embodiments, at least 25% of all the lysine side chains within the polypeptide are substituted with —$C(O)R^2$, —$C(O)R^3$, or a combination thereof.

As noted above, the polypeptide may be gelatin, and gelatin contains lysine side chains as pendant groups from the polypeptide backbone. In some embodiments, from about 5% to 100% of the lysine side chains in the gelatin are substituted. In general, any polypeptide may be derivatized with the polyunsaturated alkenyl groups. Where any such polypeptides include lysine side chains pendant from the polypeptide, from about 5% to 100% of the lysine side chains are substituted. This may include about 5%, about 15%, about 25%, about 35%, about 45%, about 55%, about 65%, about 75%, about 85%, about 95%, and ranges between any two of these values, of the lysine side chains being substituted with a $C_8$-$C_{24}$ polyunsaturated alkenyl group. In some embodiments, at least 10% of the lysine side chains are substituted with $C_8$-$C_{24}$ polyunsaturated alkenyl groups. In some embodiments, at least 25% of the lysine side chains are substituted with the $C_8$-$C_{24}$ polyunsaturated alkenyl groups.

In accordance with another aspect, compositions are provided that include any of the polypeptides described herein. The compositions may include, but are not limited to, paints, coatings, polymers, and the like. Such compositions include a polypeptide and at least one additive known in the art. Examples of suitable additives for use in the compositions include, but are not limited to, driers, pigments, leveling agents, flatting agents, dispersing agents, flow control agents, ultraviolet (UV) absorbers, plasticizers and solvents. Specific examples of such additives can be found in Raw Materials Index, published by the National Paint & Coatings Association, 1500 R.I. Avenue, N.W., Washington, D.C. 20005.

Illustrative driers include, but are not limited to, various salts of cobalt, iron, manganese, cobalt, lead, manganese, calcium, zinc, zirconium, bismuth, lithium, aluminum, barium, cerium, vanadium, lanthanum, neodymium, iron, sodium, or potassium, or combinations thereof. The driers may include as the salt octoates or naphthenates, in an amount of about 0.005 wt. % to about 0.5 wt. % metal, based on the polypeptide. A description of metal driers, their functions, and methods for using them may be found in Handbook of Coatings Additives, p. 496-506, ed. by L. J. Calbo, Marcel Dekker, New York, N.Y., 1987.

Where the composition includes a pigment, the pigments may be organic or inorganic, including those set forth by the Colour Index, 3d Ed., 2d Rev., 1982, published by the Society of Dyers and Colourists in association with the American Association of Textile Chemists and Colorists. Other examples of suitable pigments include, but are not limited to, titanium dioxide, barytes, clay, calcium carbonate, CI Pigment White 6 (titanium dioxide), CI Pigment Red 101 (red iron oxide), CI Pigment Yellow 42, CI Pigment Blue (copper phthalocyanines); CI Pigment Red 49:1 and CI Pigment Red 57:1. Colorants such as, for example, phthalocyanine blue, molybdate orange, or carbon black, may be added to the a formulation.

Where the composition includes a leveling agent, illustrative agents include, but are not limited to, silicones, fluorocarbons, cellulosics, extenders, plasticizers, and combinations thereof. Where the composition includes a flatteing agent, illustrative agents include, but are not limited to, synthetic silica, and synthetic silicate.

Where the composition includes a dispersing agent, illustrative agents include, but are not limited to, sodium bis (tridecyl) sulfosuccinate, di(2-ethyl hexyl) sodium sulfosuccinate, sodium dihexylsulfosuccinate, sodium dicyclohexyl sulfosuccinate, diamyl sodium sulfosuccinate, sodium diisobutyl sulfosuccinate, disodium iso-decyl sulfosuccinate, disodium ethoxylated alcohol half ester of sulfosuccinic acid, disodium alkyl amido polyethoxy sulfosuccinate, tetra-sodium N-(1,2-dicarboxyethyl)-N-octadecyl sulfosuccinamate, disodium N-octasulfosuccinamate, and sulfated ethoxylated nonylphenol, 2-amino-2-methyl-1-propanol.

Where the composition includes a flow control agent, illustrative agents include, but are not limited to, polyaminoamide phosphate, high molecular weight carboxylic acid salts of polyamine amides, and alkylene amine salts of an unsaturated fatty acid. Further examples include, but are not limited to, polysiloxane copolymers, polyacrylate solution, cellulose esters, hydroxyethyl cellulose, hydroxypropyl cellulose, polyamide wax, polyolefin wax, hydroxypropyl methyl cellulose, and polyethylene oxide.

Where the composition includes an ultraviolet (UV) absorber, illustrative absorbers include, but are not limited to, substituted benzophenone, substituted benzotriazoles, hindered amines, and hindered benzoates, diethyl-3-acetyl-4-hydroxy-benzyl-phosphonate, 4-dodecyloxy-2-hydroxy benzophenone, and resorcinol monobenzoate.

Where the composition includes a plasticizer, illustrative plasticizers include, but are not limited to mono $C_8$-$C_{24}$ fatty acids, $C_8$-$C_{24}$ saturated fatty acids, and phthalate esters such as di-2-ethyl hexyl phthalate (DEHP), diisodecyl phthalate (DIDP), diisononyl phthalate (DINP), and benzylbutylphthalate (BBP).

Illustrative solvents for use in the compositions include both aqueous and non-aqueous solvent. For example, water and organic solvents may be used. Illustrative organic solvents include, but are not limited to, ethanol, n-propanol, isopropanol, n-butanol, sec-butanol, isobutanol, ethylene glycol, monobutyl ether, propylene glycol n-butyl ether, propylene glycol methyl ether, propylene glycol monopropyl ether, dipropylene glycol methyl ether, diethylene glycol monobutyl ether, methylene chloride (dichloromethane), 1,1,1-trichloroethane (methyl chloroform), 1,1,2-trichloro-1,2,2-trifluoroethane (CFC-113), trichlorofluoromethane (CFC-11), dichlorodifluoromethane (CFC-12), chlorodifluoromethane (HCFC-22), trifluoromethane (HFC-23), 1,2-dichloro-1,1,2,2-tetrafluoroethane (CFC-114), chloropentafluoroethane (CFC-115), 1,1,1-trifluoro 2,2-dichloroethane (HCFC-123), 1,1,1,2-tetrafluoroethane (HCFC-134a), 1,1-dichloro-1-fluoroethane (HCFC-141b), 1-chloro-1,1-difluoroethane (HCFC-142b), 2-chloro-1,1,1,2-tetrafluoroethane (HCFC-124), pentafluoroethane (HFC-125), 1,1,2,2-tetrafluoroethane (HFC-134), 1,1,1-trifluuoroethane (HFC-143a), 1,1-difluoroethane (HFC-152a), parachlorobenzotrifluoride (PCBTF), cyclic, branched, or linear completely methylated siloxanes, acetone, perchloroethylene (tetrachloroethylene), 3,3-dichloro-1,1,1,2,2-pentafluoropropane (HCFC-225ca), 1,3-dichloro-1,1,2,2,3-pentafluoropropane (HCFC-225cb), 1,1,1,2,3,4,4,5,5,5-decafluoropentane (HFC-43-10mee), difluoromethane (HFC-32), ethylfluoride (HFC-161), 1,1,1,3,3,3-hexafluoropropane (HFC-236fa), 1,1,2,2,3-pentafluoropropane (HFC-245ca), 1,1,2,3,3-pentafluoropropane (HFC-245ea), 1,1,1,2,3-pentafluoropropane (HFC-245eb), 1,1,1,3,3-pentafluoropropane (HFC-245fa), 1,1,1,2,3,3-hexafluoropropane (HFC-236ea), 1,1,1,3,3-pentafluorobutane (HFC-365-mfc), chlorofluoromethane (HCFC-31), 1-chloro-1-fluoroethane (HCFC-151a), 1,2-dichloro-1,1,2-trifluoroethane (HCFC-123a), 1,1,1,2,2,3,3,4,4-nonafluoro-4-methoxy-butane ($C_4F_9OCH_3$), 2-(difluoromethoxymethyl)-1,1,1,2,3,3,3-heptafluoropropane (($CF_3)_2$CFCF$_2$OCH$_3$), and 1-ethoxy-1,1,2,2,3,3,4,4,4-nonafluorobutane.

As noted, the polypeptides may be used in a wide variety of applications. For example, the polypeptides may be used in adhesives, thermoplastics, coatings, epoxy resins, drying oils, paper products, printing inks, clothing coatings, encapsulants for organo electronics, color filters for liquid crystal display (LCD) screens and food additives.

Adhesives are widely used, for example, by the food packaging industry, especially for packages made from paper. However, most of the adhesives used in the food packaging industry are potentially toxic, as they are based upon polymeric urethanes, bisphenol-A epoxides, and rubber latex emulsions. Generally, these materials are poorly compatible with the environment. Any of the polypeptides herein may be used as non-toxic and biodegradable adhesives. Where the polypeptide is used as an adhesive, the adhesive may be formulated as water emulsion. The emulsion may be applied to an article to form a tacky film, which as cross-links forms, the adhesive may bind two surfaces together.

The polypeptides may be used as a thermoplastic. Thermoplastics containing the polypeptides, prior to cross-linking, will flow like conventional thermoplastics, but set they into rigid structures after they cure (i.e. form cross-links). This property allows the polypeptides to be injection molded and formed into shapes that will set after the polypeptides cure. As one example, the polypeptides may be used to make thermoplastic articles that will have food contact. For example, conventional thermoplastic dinner trays have the disadvantage of leaching potentially toxic chemicals into foods and beverages when they are heated, for example, in a microwave oven. Whereas, the dinner trays made from the polypeptides are non-toxic and do not leach harmful chemicals when heated. Further, the polypeptides are robust thermoplastics that are resistant to degradation, because the peptide backbone is joined by amide bonds that are resistant to hydrolysis. In some embodiments, the polypeptides are incorporated into a thermoplastic material that includes at least one of a polyacrylate, a polymethacrylate, a polyolefin, a polyepoxy, a polyurethane, or a polyurea.

The polypeptides may also be used in other packaging, container, and plastic goods applications. For example, the polymers produced by curing of the polypeptide through cross-linking, may be used in wide variety of plastics for any application such as food, beverage, or consumer packaging, sport drink bottles, freeze vacuum containers, shipping cartons, bags, optical lenses, utensils, plates, toys, furniture coatings, automobile plastic components, fiberglass, cookware, plastic utensils, computers (e.g., tablets, laptops, netbooks) computer components, medical implants, mobile electronics, phones, calculators, paneling, fibers, insulation, seats, tables, shelves, table tops, counters and the like.

The polypeptides can be used as coatings. For example, polypeptides described herein can be combined with inks and used as coatings or to illustrate the exterior of a product package (e.g., cereal box, candy wrapper, etc.).

The polymers formed by cross-linking of the polypeptides are amenable to forming into a wide variety of articles as introduced above. The polymers may be formed into articles using techniques such as blowing, compaction molding, compression molding, injection molding, extrusion, rotomolding, vacuum molding, thermoforming, and the like as are known in the art.

Thus, in accordance with another aspect, an article is provided where the article includes a polymer of any of the polypeptides described above. For example, the article may include a polypeptide described herein, where the polypeptide includes two or more groups of formula —$R^1$—$C(O)R^2$, where $R^1$ is an amino acid side chain, $R^2$ is a $C_8$-$C_{24}$ polyunsaturated alkenyl group, the polypeptide is a gelatin. The polypeptides may include amino acid side chains that are substituted with $C_8$-$C_{24}$ polyunsaturated alkenyl groups. In some embodiments the article includes a peptide that further includes one or more groups of formula —$R^1$—$C(O)R^3$ and $R^3$ is a $C_8$-$C_{24}$ monounsaturated alkenyl group, $C_8$-$C_{24}$ alkyl group, or a combination thereof. In some embodiments, at least two $R^2$ groups are crosslinked by a bond, O, O—O, or a combination thereof. In some embodiments, the article is a packaging for a comestible. In some embodiments, the packaging is a coating, can, box, tray, liner, or wrapper.

In another aspect, a method is provided for coating an article with any of the above polypeptides. The method includes contacting the article with a polypeptide and exposing the article and polypeptide to air for a time sufficient to cure and cross-link the polypeptide. Because the polypeptides contain $C_8$-$C_{24}$ polyunsaturated alkenyl groups, the polypeptides may cure to a hardened coating upon exposure to the air upon cross-linking of the alkenyl groups. In some embodiments, the method includes contacting the article with a polypeptide, where the polypeptide includes two or more groups of formula —$R^1$—$C(O)R^2$, $R^1$ is an amino acid side chain, $R^2$ is a $C_8$-$C_{24}$ polyunsaturated alkenyl group, and the polypeptide is a gelatin; and exposing the article to air until at least two $R^2$ groups are crosslinked by a bond, O, O—O, or a combination thereof, to form the coated article. The method may also include applying heat in addition to exposing the article to air. The heat will accelerate the cross-linking process and drive off any carrier solvents that may be used to coat the article with the polypeptide. In some embodiments, the heating is conducted at a temperature of about 30° C. to about 200° C. Specific temperatures include about 30° C., about 50° C., about 75° C., about 100° C., about 125° C., about 150° C., about 175° C., about 200° C., and ranges between any two of these temperatures.

The method may also include contacting the polypeptide with a metal catalyst drier. Representative metals include cobalt, iron, manganese, cobalt, lead, manganese, calcium, zinc, zirconium, bismuth, lithium, aluminum, barium, cerium, vanadium, lanthanum, neodymium, iron, sodium, or potassium, or combinations thereof.

The polypeptide used in the method of coating an article, may be formulated into a coating composition as described above. This includes dissolving or suspending the polypeptide in an aqueous or non-aqueous solvent, and adding coating additives. For example, the solvent may be water, or an organic solvent. Suitable additives includes but are not limited to, driers, pigments, leveling agents, flatting agents, dispersing agents, flow control agents, ultraviolet (UV) absorbers, plasticizers and solvents.

The present technology, thus generally described, will be understood more readily by reference to the following Examples, which are provided by way of illustration and is not intended to be limiting of the present technology.

EXAMPLES

Example 1

Synthesis of gelatin alkyd peptides. As shown in Scheme 1, above, gelatin derivative 1.5 is prepared from peptide 1.1. The modification of only a single amino acid side is shown in routes a, b, and c of Scheme 1, but numerous amino chains within the peptide are modified by the procedures of routes a, b, and c. Peptide 1.1 is modified according to conventional techniques such as the reaction with gelatin derivative 1.2 (route a), dehydration with fatty acid 1.3 and a peptide coupling agent (e.g., 2-dimethylamino-ethyl-propyl-carbodiimide (EDC) or dicyclohexylcarbodiimide (DCC) (route b), or upon base (e.g., $K_2CO_3$) mediated displacement of acyl chloride 1.4 (route c). These reactions can be performed in the absence or presence of a solvent (e.g., tetrahydrofuran, dimethylformamide, $CH_2Cl_2$ etc.) at a temperature of about 25° C. to about 100° C. Upon exposure to air at room temperature, polymer 1.5 develops crosslinks among the $C_8$-$C_{24}$ polyunsaturated alkenyl groups at $R_1$.

Example 2

Synthesis of Gelatin Alkyd Peptides from Acid Chlorides.
Stock Solution of Aqueous Gelatin:

Solutions A, B, and C of gelatin alkyd peptides in water are prepared by dissolving gelatin (10 g, having approximately 13% by weight of amino acids with amino functional groups) into water (200 mL) at 50° C. and cooling the solution to room temperature. To this solution is added sodium carbonate (2.94 g) with stirring.

Reaction A:

Reaction A employs approximately one molar equivalent of an omega-3 acid chloride relative to the amino functional groups in the gelatin solution. An omega-3 acid chloride 2.218 g (7.471 mmol) is dissolved into 50 mL of hexanes and the hexane solution is added drop-wise onto the stock solution of aqueous gelatin to form an organic layer on top the aqueous phase. The two layers are stirred for 5 hours at room temperature and the aqueous phase is separated from the hexanes.

Reaction B:

Reaction B employs approximately ½ of a molar equivalent of omega-3 acid chloride relative to the amino functional groups in the gelatin solution. An omega-3 acid chloride 1.109 g (3.735 mmol) is dissolved into 25 mL of hexanes and the solution is added drop-wise onto the stock solution of aqueous gelatin to form an organic layer on top the aqueous phase. The two layers are stirred for 5 hours at room temperature and the aqueous phase is separated from the hexanes.

Reaction C:

Reaction C employs approximately ¼ of a molar equivalent of omega-3 acid chloride relative to the amino functional groups in the gelatin solution. An omega-3 acid chloride 0.555 g (1.868 mmol) is dissolved into 15 mL of hexanes and the solution is added drop-wise onto the stock solution of aqueous gelatin to form an organic layer on top the aqueous phase. The two layers are stirred for 5 hours at room temperature and the aqueous phase is separated from the hexanes.

Example 3

Coating Articles with Gelatin Alkyd Peptides.

An aqueous dispersion of gelatin alkyd peptide 1.5 is prepared where $R_1$ is, for example, the carbon chain from all-cis-9,12,15-linolenic acid, and the gelatin alkyd peptide has a molecular weight of about 25,000 Daltons. The dispersion is coated within the interior of an aluminum can for storing vegetables. The coated can is heated to 50° C. in air for thirty minutes as the degree of cross-linking within the gelatin alkyd peptide increases. The gelatin alkyd peptide coating exhibits rapid dry time, good resistance to picking up dirt, and good exterior durability. Additionally, the gelatin alkyd peptide coatings do not leach toxic chemicals into food when heated. Rather, the gelatin alkyd peptide coatings non-toxic and thus suitable for use with food and beverage containers.

Example 4

Ink Formulation.

An alkyd mineral oil dispersion is prepared where $R_1$ is, for example, the carbon chain from all-cis-9,12,15-linolenic acid (20% by weight) and the gelatin alkyd peptide has a molecular weight of about 25,000 Daltons. To the alkyd mineral oil dispersion is added carbon black, reflex blue pigments and an asphaltum solution. A representative formulation is shown below in Table 1:

TABLE 1

| Component | Wt % |
| --- | --- |
| Carbon black (CI P. Black 7) | 19.0 |
| Reflex blue (CI P. Blue 18) | 2.0 |
| 70 Pa s mineral oil | 55.0 |
| 0.05 Pa s mineral oil | 9.0 |
| Gelatin Omega-3 Alkyd | 10.0 |
| Drying Catalysts | 2.5 |
| Asphaltum solution | 2.5 |

The formulation is coated, for example, onto paper products and used as an ink. The gelatin alkyd peptide coating exhibits rapid dry time, good resistance to picking up dirt, and good abrasion resistance, and exterior durability. Additionally, the gelatin alkyd peptide coatings do not leach toxic chemicals and degrade into non-toxic by products. Rather, the gelatin alkyd peptide coatings are non-toxic and thus suitable for use with a wide variety of paper products. The gelatin alkyd peptide coatings can similarly be incorporated into printing inks of various colors, clothing coatings, encapsulants for organo electronics, and color filters for liquid crystal display (LCD) screens.

EQUIVALENTS

The embodiments, illustratively described herein may suitably be practiced in the absence of any element or elements, limitation or limitations, not specifically disclosed herein. Thus, for example, the terms 'comprising,' 'including,' 'containing,' etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase 'consisting essentially of' will be understood to include those elements specifically recited and those additional elements that do not materially affect the basic and novel characteristics of the claimed technology. The phrase 'consisting of' excludes any element not specified.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent compositions, apparatuses, and methods within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as 'up to,' 'at least,' 'greater than,' 'less than,' and the like, include the number recited and refer to ranges which can be subsequently broken down into subranges as discussed above. Similarly, the phrase "at least about" some value such as, e.g., wt % includes at least the value and about the value. For example "at least about 1 wt %" means "at least 1 wt % or about 1 wt %." Finally, as will be understood by one skilled in the art, a range includes each individual member.

While certain embodiments have been illustrated and described, it should be understood that changes and modifications can be made therein in accordance with ordinary skill in the art without departing from the technology in its broader aspects as defined in the following claims.

What is claimed is:

1. A polypeptide comprising one or more groups of formula $-R^1-C(O)R^2$, wherein $R^1$ is an amino acid side chain, $R^2$ is a $C_8$-$C_{24}$ polyunsaturated alkenyl group, and the polypeptide is a gelatin.

2. The polypeptide of claim 1, further comprising one or more groups of formula $R^1$—$C(O)R^3$, wherein $R^3$ is a $C_8$-$C_{24}$ monounsaturated alkenyl group, $C_8$-$C_{24}$ alkyl group, or a combination thereof.

3. The polypeptide of claim 1, having at least one intramolecular crosslink, wherein each intramolecular crosslink comprises two $R^2$ groups within the polypeptide that are joined by a bond, O, O—O, or a combination thereof.

4. The polypeptide of claim 3, wherein each intermolecular crosslink comprises a first $R^2$ group from the polypeptide and a second $R^2$ group from another such polypeptide, wherein the first and second $R^2$ groups are joined by a bond, O, O—O, or a combination thereof.

5. The polypeptide of claim 3, wherein the crosslink comprises a moiety selected from the group consisting of:

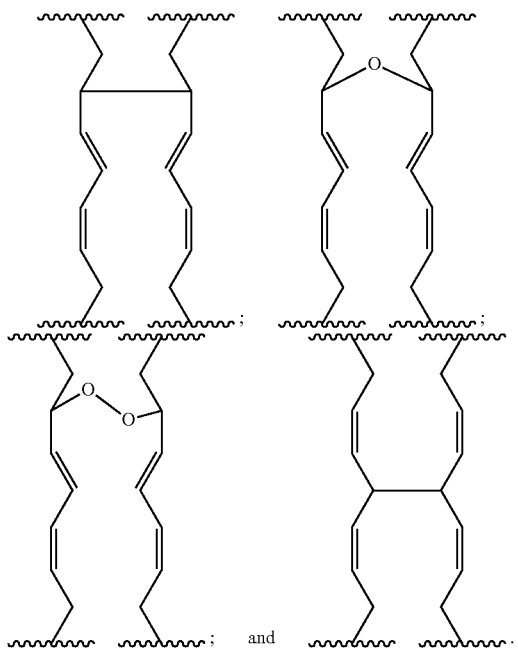

6. The polypeptide of claim 1, wherein the polypeptide comprises about 5 wt % to about 20 wt % hydroxyproline.

7. The polypeptide of claim 1, wherein the polypeptide has a weight average molecular weight of about 10,000 Daltons to about 500,000 Daltons.

8. The polypeptide of claim 1, wherein the polypeptide has a weight average molecular weight of about 50,000 Daltons to about 100,000 Daltons.

9. The polypeptide of claim 1, wherein $R^1$ is the amino acid side chain from lysine, arginine, histidine, serine, threonine, asparagine, glutamine, cysteine, selenocysteine, tyrosine, or tryptophan.

10. The polypeptide of claim 1, wherein $R^1$ is the amino acid side chain from lysine.

11. The polypeptide of claim 1, wherein the polypeptide comprises lysine side chains and at least 10% of all the lysine side chains within the polypeptide are substituted with —$C(O)R^2$, —$C(O)R^3$, or a combination thereof.

12. The polypeptide of claim 1, wherein the polypeptide comprises lysine side chains and at least 25% of all the lysine side chains within the polypeptide are substituted with —$C(O)R^2$, —$C(O)R^3$, or a combination thereof.

13. The polypeptide of claim 1, wherein —$C(O)R^2$ derives from a fatty acid, wherein the fatty acid is hexadecatrienoic acid, linoleic acid, α-linolenic acid, stearidonic acid, eicosatrienoic acid, eicosatetraenoic acid, eicosapentenoic acid, heneicosapentenoic acid, docosapentenoic acid, docosahexaenoic acid, tetracosapentenoic acid, tetracosahexaenoic acid, or a combination thereof.

14. The polypeptide of claim 13, wherein the fatty acid is linoleic acid, α-linolenic acid or a combination thereof.

15. The polypeptide of claim 1, wherein —$C(O)R^2$ derives from an omega-3 fatty acid.

16. The polypeptide of claim 1, wherein —$C(O)R^2$ derives from an all-cis $C_8$-$C_{24}$ polyunsaturated alkenyl group.

17. The polypeptide of claim 16, wherein the all-cis $C_8$-$C_{24}$ polyunsaturated alkenyl group derives from all-cis-7,10,13-hexadecatrienoic acid, all-cis-9,12-linoleic acid, all-cis-9,12,15-octadecatrienoic acid, all-cis-6,9,12,15-octadecatetraenoic acid, all-cis 11,14,17 eicosatrienoic acid, all-cis-8,11,14,17-eicosatetraenoic acid, all-cis-5,8,11,14,17-eicosapentenoic acid, all-cis-6,9,12,15,18-heneicosapentenoic acid, all-cis-7,10,13,16,19-docosapentenoic acid, all-cis-4,7,10,13,16,19-docosahexaenoic acid, all-cis-9,12,15,18,21-tetracosapentenoic acid, all-cis-6,9,12,15,18,21-tetracosahexaenoic acid, or a combination thereof.

18. The polypeptide of claim 16, wherein the all-cis $C_8$-$C_{24}$ polyunsaturated alkenyl group derives from all-cis-9,12-linoleic acid, all-cis-9,12,15-octadecatrienoic acid, or a combination thereof.

19. The polypeptide of claim 2, wherein —$C(O)R^3$ derives from oleic acid, palmitoleic acid, or vaccenic acid.

20. The polypeptide of claim 2, wherein —$C(O)R^3$ derives from lauric acid, myristic acid, palmitic acid, stearic acid, or a combination thereof.

21. The polypeptide of claim 1 which is an epoxy resin, an adhesive, thermoplastic, coating, or drying oil.

22. A composition comprising of the polypeptide of claim 1 and at least one drier, pigment, leveling agent, flatting agent, dispersing agent, flow control agent, ultraviolet (UV) absorber, plasticizer or combination thereof.

23. An article comprising a polypeptide, wherein the polypeptide comprises two or more groups of formula —$R^1$—$C(O)R^2$, wherein $R^1$ is an amino acid side chain, $R^2$ is a $C_8$-$C_{24}$ polyunsaturated alkenyl group, the polypeptide is a gelatin, and wherein the article comprises packaging for a comestible.

24. The article of claim 23, wherein the peptide further comprises one or more groups of formula —$R^1$—$C(O)R^3$ and $R^3$ is a $C_8$-$C_{24}$ monounsaturated alkenyl group, $C_8$-$C_{24}$ alkyl group, or a combination thereof.

25. The article of claim 23, wherein at least two $R^2$ groups are crosslinked by a bond, O, O—O, or a combination thereof.

26. The article of claim 23, wherein the packaging is a can, box, tray, liner, or wrapper.

27. A method of coating an article, the method comprising:
contacting the article with a polypeptide, wherein the polypeptide comprises two or more groups of formula —$R^1$—$C(O)R^2$, wherein $R^1$ is an amino acid side chain, $R^2$ is a $C_8$-$C_{24}$ polyunsaturated alkenyl group, and the polypeptide is a gelatin; and
exposing the article to air until at least two $R^2$ groups are crosslinked by a bond, O, O—O, or a combination thereof, to form the coated article.

28. The method of claim 27, further comprising heating the coated article to a temperature of about 30° C. to about 80° C.

29. The method of claim 27, further comprising contacting the polypeptide with a metal catalyst drier.

30. The method of claim 29, wherein the metal is cobalt, iron, manganese, cobalt, lead, manganese, calcium, zinc, zirconium, bismuth, lithium, aluminum, barium, cerium, vanadium, lanthanum, neodymium, iron, sodium, or potassium, or combinations thereof.

* * * * *

UNITED STATES PATENT AND TRADEMARK OFFICE
CERTIFICATE OF CORRECTION

PATENT NO. : 8,859,735 B2  
APPLICATION NO. : 13/885306  
DATED : October 14, 2014  
INVENTOR(S) : Carlson et al.

Page 1 of 1

It is certified that error appears in the above-identified patent and that said Letters Patent is hereby corrected as shown below:

In the Specification

In Column 1, Line 10, delete "U.S. national phase application of International Application Serial No. PCT/US2012/052465, filed on Aug. 27, 2012," and
insert -- U.S. national stage filing under 35 U.S.C. §371 of International Application Serial No. PCT/US2012/052465, filed on Aug. 27, 2012, --, therefor.

In Column 8, Line 63, delete "cobalt, iron, manganese, cobalt, lead, manganese," and insert -- cobalt, iron, manganese, lead, --, therefor.

In Column 9, Line 22, delete "flatteing" and insert -- flatting --, therefor.

In Column 10, Line 10, delete "trifluuoroethane" and insert -- trifluoroethane --, therefor.

In Column 11, Line 67, delete "cobalt, iron, manganese, cobalt, lead, manganese," and insert -- cobalt, iron, manganese, lead, --, therefor.

In the Claims

In Column 16, Line 32, in Claim 22, delete "comprising of" and insert -- comprising --, therefor.

In Column 16, Lines 61-62, Claim 30, delete "cobalt, iron, manganese, cobalt, lead, manganese," and insert -- cobalt, iron, manganese, lead, --, therefor.

Signed and Sealed this  
Twenty-sixth Day of May, 2015

Michelle K. Lee  
*Director of the United States Patent and Trademark Office*